United States Patent
Kusakabe et al.

(10) Patent No.: US 11,117,725 B2
(45) Date of Patent: Sep. 14, 2021

(54) PACKAGING MATERIAL FOR STERILIZATION

(71) Applicant: Asahi Kasei Kabushiki Kaisha, Tokyo (JP)

(72) Inventors: Junichi Kusakabe, Tokyo (JP); Masaaki Mori, Tokyo (JP); Seiichi Amano, Tokyo (JP); Kazufumi Kato, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 188 days.

(21) Appl. No.: 16/079,585

(22) PCT Filed: Feb. 21, 2017

(86) PCT No.: PCT/JP2017/006381
§ 371 (c)(1),
(2) Date: Aug. 24, 2018

(87) PCT Pub. No.: WO2017/146050
PCT Pub. Date: Aug. 31, 2017

(65) Prior Publication Data
US 2019/0071228 A1 Mar. 7, 2019

(30) Foreign Application Priority Data
Feb. 25, 2016 (JP) .............................. JP2016-034034

(51) Int. Cl.
| *B65D 65/40* | (2006.01) |
| *D04H 3/16* | (2006.01) |
| *B32B 5/26* | (2006.01) |
| *B32B 5/02* | (2006.01) |
| *A61F 13/00* | (2006.01) |
| *B32B 7/14* | (2006.01) |
| *A61B 50/30* | (2016.01) |
| *B32B 27/08* | (2006.01) |
| *B32B 27/12* | (2006.01) |
| *B32B 27/32* | (2006.01) |
| *B32B 27/36* | (2006.01) |
| *B32B 38/18* | (2006.01) |

(52) U.S. Cl.
CPC .............. *B65D 65/40* (2013.01); *A61B 50/30* (2016.02); *A61F 13/00072* (2013.01); *B32B 5/022* (2013.01); *B32B 5/26* (2013.01); *B32B 7/14* (2013.01); *D04H 3/16* (2013.01); *B32B 27/08* (2013.01); *B32B 27/12* (2013.01); *B32B 27/32* (2013.01); *B32B 27/36* (2013.01); *B32B 38/18* (2013.01); *B32B 2250/02* (2013.01); *B32B 2255/02* (2013.01); *B32B 2262/0253* (2013.01); *B32B 2262/0276* (2013.01); *B32B 2262/0284* (2013.01); *B32B 2307/306* (2013.01); *B32B 2307/308* (2013.01); *B32B 2307/31* (2013.01); *B32B 2307/54* (2013.01); *B32B 2307/5825* (2013.01); *B32B 2307/718* (2013.01); *B32B 2307/7145* (2013.01); *B32B 2307/724* (2013.01); *B32B 2307/7244* (2013.01); *B32B 2307/7265* (2013.01); *B32B 2307/734* (2013.01); *B32B 2439/80* (2013.01); *Y10T 428/1352* (2015.01)

(58) Field of Classification Search
CPC ........ B32B 2255/02; B32B 2262/0253; B32B 2262/0276; B32B 2262/0284; B32B 2307/306; B32B 2307/308; B32B 2307/31; B32B 2307/54; B32B 2307/5825; B32B 2307/7145; B32B 2307/718; B32B 2307/724; B32B 2307/7244; B32B 2307/7265; B32B 2307/734; B32B 2439/80; B32B 27/08; B32B 27/12; B32B 27/32; B32B 27/36; B32B 38/18; B32B 5/022; B32B 5/26; B32B 7/14; A61B 50/30; A61F 13/00072; B65D 65/40; D04H 3/16
See application file for complete search history.

(56) References Cited

U.S. PATENT DOCUMENTS

| 4,196,245 A | 4/1980 | Kitson et al. |
| 8,513,148 B2 | 8/2013 | Irie et al. |
(Continued)

FOREIGN PATENT DOCUMENTS

| EP | 1637317 A1 | 3/2006 |
| EP | 2022879 A1 | 2/2009 |
| EP | 2896731 A1 | 7/2015 |
| JP | H07-238449 A | 9/1995 |
(Continued)

OTHER PUBLICATIONS

International Search Report issued in corresponding International Patent Application No. PCT/JP2017/006381 dated Apr. 11, 2017.
(Continued)

*Primary Examiner* — Yan Lan
(74) *Attorney, Agent, or Firm* — Morgan, Lewis & Bockius LLP

(57) ABSTRACT

The present invention provides a novel packaging material for sterilization which has processing suitability as a packaging material, is compatible with all sterilization processing methods such as those performed under high-temperature conditions, has small variation in shapes and dimensions, and is capable of maintaining an internal sterilized condition. This packaging material for sterilization is configured from at least two layers of laminated non-woven fabrics comprising a non-woven fabric layer (I) formed of continuous long fibers having an average fiber diameter of 5-30 μm and a non-woven fabric layer (II) formed of ultra-fine fibers having an average fiber diameter of 0.1-4 μm.

19 Claims, No Drawings

(56) References Cited

U.S. PATENT DOCUMENTS

2012/0045626 A1   2/2012   Inokuma et al.
2013/0269294 A1   10/2013  Benton et al.

FOREIGN PATENT DOCUMENTS

| JP | 2011-036763 A | 2/2011 |
| JP | 2014-237478 A | 12/2014 |
| JP | 3195730 U | 1/2015 |
| TW | I349614 A | 10/2011 |
| WO | 2010/126109 A1 | 11/2010 |

OTHER PUBLICATIONS

International Preliminary Report on Patentability and Written Opinion issued in corresponding International Patent Application No. PCT/JP2017/006381 dated Sep. 7, 2018.
Supplemental European Search Report issued in related European Patent Application No. 17756488.7 dated Dec. 17, 2018.

PACKAGING MATERIAL FOR STERILIZATION

FIELD

The present invention relates to a packaging material for sterilization, to be used for sterilization of medical equipment, for example.

BACKGROUND

The concept of using medical equipment after sterilization processing to prevent infectious disease is already known, and equipment that is subjected to such processing includes, specifically, sondes, scalpels, pincettes, scissors and the like. High-temperature, high-pressure vapor methods and ethylene oxide gas methods are used as sterilization processing methods, and equipment packaging materials suitable for such processing methods are used. Fibrous sheets suitable as packaging materials for sterilization must have satisfactory air permeability, a small pore size and bubble point, with satisfactory barrier properties, heat sealability, and satisfactory napping properties.

Packaging materials for sterilization generally employ nonwoven fabrics or films that have pulp or synthetic fibers such as polyethylene as the starting material, but in recent years, combinations of nonwoven fabrics or transparent resin films are used by being bonded together in the form of bags, allowing the inside to be visible.

For example, PTL 1 listed below describes a nonwoven fabric prepared by a flash-spinning method using a polyethylene resin, as a fibrous sheet to be used in the medical field. In flash-spinning, the yarn diameter is non-uniform, production is not possible with an average fiber diameter of 2 μm or smaller, the basis weight dispersibility is unsatisfactory and the use of a solvent or the like is necessary, such factors therefore making it impractical in terms of safety as well.

PTL 2 listed below describes a pulp-type sterilized sheet, wherein the sterilized sheet and a synthetic resin film are laminated to obtain heat sealability. However, usually when a pulp sheet is used in a packaging material for sterilization, paper dust flies off during working because the fibers are not connected one to another unlike in a long filament nonwoven fabric, and this has been a crucial problem for medical equipment. In addition, in environments where alcohol or water are frequently used, pulp sterilized sheets are extremely fragile and unacceptable as packaging materials.

CITATION LIST

Patent Literature

[PTL 1] Japanese Unexamined Patent Publication No. 2014-237478
[PTL 2] Japanese Unexamined Patent Publication HEI No. 7-238449

SUMMARY

Technical Problem

In light of the prior art mentioned above, the problem to be solved by the present invention is that of providing a novel packaging material for sterilization which has processing suitability as a packaging material, is compatible with all sterilization processing methods such as those performed under high-temperature conditions, has low variation in shape and dimensions, and can maintain an internal sterilized condition.

Solution to Problem

As a result of conducting diligent research and experimentation with the aim of solving the aforementioned problem, the present inventors have found that by using a nonwoven fabric having the structure specified below, it is possible to obtain a packaging material for sterilization with higher productivity and higher performance, and the invention has been completed upon this finding. Specifically, the present invention is as follows.

[1] A packaging material for sterilization constructed of a layered nonwoven fabric with at least two layers, comprising a nonwoven fabric layer (I) formed of continuous long fibers having an average fiber diameter of 5 to 30 μm and a nonwoven fabric layer (II) formed of ultrafine fibers having an average fiber diameter of 0.1 to 4 μm.

[2] The packaging material for sterilization according to [1] above, wherein an interlayer formed of the nonwoven fabric layer (II) is disposed between two layers of the nonwoven fabric layer (I).

[3] The packaging material for sterilization according to [1] or [2] above, wherein the nonwoven fabric layer (II) is composed of a melt-blown nonwoven fabric.

[4] The packaging material for sterilization according to any one of [1] to [3] above, wherein the average flow pore size of the layered nonwoven fabric is 0.1 to 30 μm, and the bubble point is 0.5 to 50 μm.

[5] The packaging material for sterilization according to any one of [1] to [4] above, wherein the basis weight of the layered nonwoven fabric is 8.0 to 100 g/m$^2$, and the thickness is 0.03 to 0.2 mm.

[6] The packaging material for sterilization according to any one of [1] to [5] above, wherein the air permeability is 1 to 100 seconds/100 ml, as determined by the time required for 100 ml of air to pass through the layered nonwoven fabric in a Gurley air permeability test.

[7] The packaging material for sterilization according to any one of [1] to [6] above, wherein the tensile strength of the layered nonwoven fabric is 10 to 300 N/25 mm width, and the puncture strength is 70 to 700 N.

[8] The packaging material for sterilization according to any one of [1] to [7] above, wherein the layered nonwoven fabric is made of polyester.

[9] The packaging material for sterilization according to any one of [1] to [8] above, wherein the specific surface area of the layered nonwoven fabric is 0.01 to 10 m$^2$/g.

Advantageous Effects of Invention

The packaging material for sterilization of the invention, having a specific structure and employing a layered nonwoven fabric with a highly controlled pore diameter, can be applied for all sterilization methods including steam sterilization, and can be produced at high yield and at low cost with stable processing steps, while its suitable air permeability and pore diameter provide a highly satisfactory bacterial barrier property that allows an internal sterilized condition to be maintained for the packaging material, and its excellent stability of quality, with minimal fly-off of paper dust and the like, provides high performance and high quality.

Embodiments of the invention will now be described in detail.

The packaging material for sterilization of this embodiment is a layered nonwoven fabric with at least two layers including an ultrafine fiber layer. A nonwoven fabric including an ultrafine fiber layer has a small pore diameter, a high specific surface area on the fiber surface, satisfactory air permeability and a high bacterial barrier property.

The nonwoven fabric layer (I) is made of fibers with fiber diameters of 5 to 30 μm. If the fiber diameter is no greater than 30 μm, the fiber diameters will not be too thick and it will be possible to obtain uniform interfiber distances, thereby allowing a compact, homogeneous nonwoven fabric laminate to be obtained, and when the nonwoven fabric layer (I) and nonwoven fabric layer (II) are layered in contact with each other, the ultrafine fibers composing the nonwoven fabric layer (II) will be more uniformly situated between the fibers composing the nonwoven fabric layer (I). This can result in uniform pore diameters in the layered nonwoven fabric, reducing the bubble point, which is the maximum pore diameter, and allowing a satisfactory bacterial barrier property to be exhibited. The nonwoven fabric layer (II) may consist of two or more layers, depending on the case. If the fiber diameters of the fibers composing the nonwoven fabric layer (I) are 5 μm or greater, on the other hand, the monofilament strength will be increased, the layered nonwoven fabric will be able to exhibit sufficient tension and puncture strength, and the processability will also be stable. From this standpoint the fiber diameters of the nonwoven fabric composing the nonwoven fabric layer (I) are preferably 7 to 20 μm and more preferably 9 to 18 μm.

The nonwoven fabric layer (II) is composed of ultrafine fibers having fiber diameters of 0.1 to 4 μm. If the fiber diameters are no greater than 4 μm, the interfiber distances will not be excessively large, micropore diameters can be obtained, and a satisfactory bacterial barrier property can be exhibited. If they are less than 0.1 μm, the nonwoven fabric will have excessively small pore diameters in the base material and may potentially exhibit poor air permeability. If they are greater than 4 μm, the denseness and pore diameter homogeneity will be lower, significantly reducing the bacterial barrier property. From this standpoint, the fiber diameters in the nonwoven fabric of the nonwoven fabric layer (II) are in the range of more preferably 0.3 to 3 μm and even more preferably 0.5 to 2.5 μm.

In order to more stably produce the packaging material for sterilization of this embodiment, a three-layer layered nonwoven fabric is preferred in which a nonwoven fabric layer (I) is situated as an interlayer between two layers of the nonwoven fabric layer (I). If both sides of the layered nonwoven fabric are the nonwoven fabric layer (I), it will be possible to minimize napping and lint generation when external force has been applied to the nonwoven fabric surface during working, while during production, defects due to surface fluff can be minimized, a satisfactory peeling property may be expected, and a nonwoven fabric can be obtained that is satisfactory as a packaging material for sterilization.

The nonwoven fabric layer (I) in the packaging material for sterilization of this embodiment is composed of a continuous long fiber nonwoven fabric. Long fibers are fibers with lengths of 15 mm and longer. Since continuous long fibers are more continuous filaments than staple fibers, they have higher monofilament strength, and as a result produce higher fabric strength and allow the production steps to be stabilized.

The packaging material for sterilization of this embodiment is preferably composed of a thermoplastic synthetic resin. For example, it may comprise a polyolefin-based resin, polyester-based resin or polyphenylene sulfide-based resin, with specific examples including polyolefins such as high-pressure method low-density polyethylene, linear low-density polyethylene (LLDPE), high-density polyethylene, polypropylene (propylene homopolymer), polypropylene random copolymer, poly(l-butene), poly(4-methyl-1-pentene) and ethylene/propylene random copolymers, which are homopolymers or copolymers of α-olefins such as ethylene, propylene, 1-butene, 1 hexene, 4-methyl-1-pentene or 1-octene, and polyesters (polyethylene terephthalate, polybutylene terephthalate or polyethylene naphthalate). Copolymers or mixtures composed mainly of these resins are also preferred. In particular, using a nonwoven fabric composed of a resin with a melting point of 140° C. or higher is suitable for sterilization processing that requires high-temperature conditions, such as steam sterilization. Polyester-based or polypropylene polymers are more preferred. Using such resins will provide especially high heat resistance, and will allow higher temperature processing than in the prior art for high-pressure steam sterilization processing that is commonly used in hospitals, and can thus reduce processing time and allow more efficient sterilization processing. This will allow a compact pore structure composed of ultrafine fibers to be maintained, and can effectively prevent infiltration of bacteria even after sterilization processing.

The method for producing each nonwoven fabric layer is not particularly restricted. The method for producing the nonwoven fabric layer (I) may be, preferably, a spunbond method, dry method or wet method. A spunbond method is more preferred for better productivity. The method for producing the nonwoven fabric layer (II) is preferably a dry method or wet method using ultrafine fibers, or it may be an electrospinning method or melt-blown method. A melt-blown method is more preferred as it will allow a superfine nonwoven fabric to be formed more easily and compactly.

The method of layering and integrating the nonwoven fabric layer (I) and nonwoven fabric layer (II) is not particularly restricted. Specifically, the method may be thermal bonding such as calendering or integration with high-temperature hot air (an air-through system), or chemical bonding such as coating of an emulsified polyacrylate or polyurethane resin. Thermal bonding, in particular, can maintain the tensile and puncture strength and bending flexibility of the nonwoven fabric, and allows formation of a plurality of nonwoven fabric layers without using a binder, and is therefore highly preferred for medical packaging materials in which inclusion of impurities is unacceptable. A particularly preferred thermal bonding method is calendering. Calendering is a method of contact bonding with a metal roll having embossed or textured irregularities, or a heated roll using a smooth flat roll. The surface pattern of a roll with surface irregularities is not particularly restricted so long as it allows the fibers to be bonded together. An easy-peeling property can be imparted by this process. The thermal bonding step may be carried out at a temperature of 50 to 120° C. lower than the melting point of the thermoplastic resin (preferably long fibers of the thermoplastic resin) and at a linear pressure of 100 to 1000 N/cm. If the linear pressure is less than 100 N/cm during the thermal bonding step it will be difficult to exhibit sufficient strength. If it exceeds 1000 N/cm, the apparent density will increase and the average flow pore size will be too small, often impairing the necessary air permeability.

The average flow pore size of the packaging material for sterilization of this embodiment is preferably 0.1 to 30 μm. If it is less than 0.1 μm, it will be unsuitable as the gaps between the fibers will be too narrow, thus lowering the air permeability, and the sterilization processing will not penetrate to the interior of the packaging material. If it exceeds 30 μm, the interfiber distance will be too large, the bacterial barrier property will be reduced and bacteria will be able to infiltrate, making it difficult to maintain a sterilized condition. For this reason as well, it is in the range of more preferably 0.3 to 20 μm and even more preferably 0.5 to 15 μm. Similar reasons also apply for the bubble point, the pore diameter being more homogeneous when the bubble point is a numerical value closer to the average flow pore size. It is in the range of preferably 0.5 to 50 μm, more preferably 2.0 to 40 μm and even more preferably 3.0 to 50 μm.

The basis weight of the packaging material for sterilization of this embodiment is preferably in the range of 8.0 to 100 g/m$^2$. If it is less than 8 g/m$^2$, the tension and puncture strength will be insufficient and the processability as a packaging material will be difficult, making it incompatible in terms of productivity. For this reason as well, it is in the range of more preferably 10 to 90 g/m$^2$ and even more preferably 15 to 80 g/m$^2$. The thickness is preferably in the range of 0.03 to 1.0 mm. If it is less than 0.03 mm, the density of the laminate will increase and the air permeability will be reduced. If it is greater than 1.0 mm, the interlayer peel strength of the nonwoven fabrics will be reduced, and it will be difficult to maintain the laminate. For this reason as well, it is in the range of more preferably 0.05 to 0.20 mm and even more preferably 0.08 to 0.15.

The air permeability of the packaging material for sterilization of this embodiment is preferably 1 to 100 seconds/100 ml, as the time required for 100 ml of air to pass through the layered nonwoven fabric in a Gurley air permeability test. If it is less than 1 second/100 ml, a small average flow pore size will not be obtainable and the bacterial barrier property will be low, which is undesirable for a packaging material for sterilization. If it exceeds 100 seconds/100 ml, the gas permeability will be poor, preventing function as a packaging material for sterilization. For this reason the air permeability is in the range of more preferably 1.0 to 80 seconds/100 ml and even more preferably 1.5 to 70 seconds/100 ml.

The tensile strength of the packaging material for sterilization of this embodiment is preferably 10 to 300 N/25 mm width. If it is less than 10 N/25 mm width, it will not be able to withstand tension during the processing steps of the production process, and deformation will readily occur when it is used as a packaging material, preventing it from functioning as a packaging material for sterilization. If it exceeds 300 N/25 mm width, the packaging material for sterilization will be too stiff and it will have poor handleability, which will prevent its functioning as a packaging material for sterilization, and for this reason it is in the range of more preferably 10 to 280 N/25 mm width and even more preferably 15 to 260 N/25 mm width. The same applies for the puncture strength, which is preferably in the range of 70 to 700 N, more preferably 15 to 650 N and even more preferably 20 to 600 N.

The specific surface area of the packaging material for sterilization of this embodiment is preferably 0.01 to 10 m$^2$/g. The mechanisms by which bacteria are trapped by a nonwoven fabric include physical trapping by the diameters of the gaps and pores between the fibers, and adsorptive trapping by static electricity and intermolecular forces. The following is a trapping method that effectively utilizes the fiber surfaces. Specifically, high air permeability can be maintained while effectively trapping bacteria that infiltrate to the interior of the packaging material, and both high sterilization efficiency and a bacterial barrier property can be exhibited. If the specific surface area is less than 0.01 m$^2$/g, the adsorption area will be small and the bacterial barrier property reduced, permitting infiltration of bacteria to the interior of the packaging material. If it is greater than 10 m$^2$/g, on the other hand, the nonwoven fabric will have excessively low air permeability in practice and it will be difficult to obtain both sterilization efficiency and a barrier property, and therefore the specific surface area is more preferably in the range of 0.05 to 9 m$^2$/g and even more preferably in the range of 0.10 to 8 m$^2$/g.

The method for producing a nonwoven fabric in this specific surface area range is not restricted. Because the purpose is to increase the area of the interface between the fibers, the specific surface area can be controlled by appropriately adjusting the diameters of the constituent fibers, for example. For melt spinning of long fibers such as meltblown fibers, however, adjacent fibers usually contact and fuse together immediately after they are discharged from the nozzle, forming apparent fiber bundles composed of several filaments and making it difficult to obtain the specified specific surface area, and therefore the conditions for polymer discharge, cooling and trapping (the throughput, temperature, airflow rate, airflow direction, etc.) may be appropriately adjusted to produce a nonwoven fabric with a high specific surface area. In addition, applying too much heat and pressure during calendering, for example, in the layering and integration may result in fusion between the fibers and a lower specific surface area, and therefore it is important to appropriately adjust the heat and pressure to achieve integration while maintaining the designed fiber shapes.

A packaging material for sterilization is generally a packaging material for sterilization with only air permeability, as in the case of a nonwoven fabric, or it employs a combination of an air-permeable base material and a non-air permeable base material such as a transparent film, and therefore heat sealability is often required for the base materials. The layered nonwoven fabric of this embodiment is composed of a thermoplastic resin and easily exhibits heat sealability. Particularly excellent heat seal strength is exhibited by employing a low-melting-point resin material or the like on one side. If heat sealability is exhibited, the layered nonwoven fabric can be used not only for packaging materials for sterilization, but also for thermocompression bond sewing for sewing of surgical gowns and the like.

The packaging material for sterilization of this embodiment is preferably subjected to water-repellent and alcohol-repellent treatment. The method for water-repellent and alcohol-repellent treatment is not restricted. For example, the method used may be a coating method in which a water-repellent material is coated, or a gas treatment method in which the fiber surfaces are activated and surface-treated by a gas having a water-repellent or alcohol-repellent property. There are no restrictions on the type of material having a water-repellent or alcohol-repellent property, or the type of gas, and fluorine-based and silicon-based materials may be mentioned.

EXAMPLES

The present invention will now be described in greater detail by examples, with the understanding that the invention is not limited to these examples.

(1) Measurement of Average Fiber Diameter (μm) of Ultrafine Fibers

A nonwoven fabric was cut to 10 cm×10 cm and vertically pressed on a steel plate at 60° C., at a pressure of 0.30 MPa for 90 seconds, after which the nonwoven fabric was vapor deposited with platinum. An SEM apparatus (JSM-6510, product of JEOL Corp.) was used for photography under conditions with an acceleration voltage of 15 kV and a working distance of 21 mm. The photographing magnification was 10,000× for filaments with average fiber diameters of less than 0.5 µm, 6000× for filaments with average fiber diameters of 0.5 or greater and less than 1.5 µm, and 4000× for filaments of 1.5 µm or greater. The visual field at each photographing magnification was 12.7 µm×9.3 µm for 10,000×, 21.1 µm×15.9 µm for 6000× and 31.7 µm×23.9 µm for 4000×. A photograph was taken of 100 random fibers, and all of their fiber diameters were photographed. However, fibers fused in the fiber length direction were excluded from the length measurement. The weight-average fiber diameter (Dw) determined by the following formula:

$$Dw=\Sigma Wi \cdot Di=\Sigma (NiDi^2)/(Ni \cdot Di)$$

{where Wi=weight percentage of fiber diameter Di=Ni·Di/ΣNi·Di} was recorded as the average fiber diameter.

(2) Basis Weight (g/m²)

Following the method of JIS L-1906, using a 20 cm length×25 cm width test piece, a total of nine locations were sampled per 1 m×1 m, at 3 locations per 1 m in the sample width direction, the masses were measured, and the average value was converted to mass per unit area.

(3) Measurement of Thickness (µm)

Following the method of JIS L-1906, the thickness was measured at 10 locations per 1 m width, and the average value was determined.

(4) Measurement of Apparent Density (g/cm³)

The basis weight (g/m²) measured in (2) above and the thickness (µm) measured in (3) above were used for calculation by the following formula:

Apparent density=(basis weight)/(thickness)

(5) Measurement of Void Percentage (%)

The apparent density (g/cm³) calculated in (4) above was used for calculation by the following formula:

Void percentage={1−(apparent density)/(resin density)}/100

(6) Measurement of Average Pore Diameter of Nonwoven Fabric

A Palm Porometer (Model CFP-1200AEX) by PMI Co. was used as the measuring apparatus. With this measuring apparatus, using a nonwoven fabric as the sample, the nonwoven fabric is immersed in a wetting liquid of known surface tension, pressure is applied to the nonwoven fabric while all of the pores of the nonwoven fabric are covered with a film of the wetting liquid, and the diameter of the pores is measured by calculation from the pressure at which the wetting liquid film breaks, and the surface tension of the wetting liquid. Using Silwick by PMI Co. as the wetting liquid, the nonwoven fabric was immersed in the wetting liquid and thoroughly deaerated, after which the pore diameter was calculated using the following formula:

$$d=C \cdot r/P$$

{where d (units: µm) is the pore diameter of the filter, r (units: N/m) is the surface tension of the wetting liquid, P (units: Pa) is the pressure at which the liquid film breaks at that pore diameter, and C is a constant determined by the wet tension and contact angle of the wetting liquid}.

The flow rate upon continuous change of the pressure P applied to the filter immersed in the wetting liquid from low pressure to high pressure (wet flow rate, units: L/min) was measured. In this measuring method, the value of the wet flow rate at a given pressure P divided by the dry flow rate at the same pressure is called the cumulative filter flow rate (units: %). The flow rate of the liquid film broken by pressure where the cumulative filter flow rate was 50% was recorded as the average flow pore size. Also, since the initial pressure does not break the liquid film even at the largest pores, that flow rate is 0. As the pressure is increased, the liquid film on the largest pores begins to break, creating a flow, and that pore diameter is called the bubble point.

(7) Specific Surface Area

Apparatus model: A Gemini2360 by Shimadzu Corp. was used.

The nonwoven fabric was rolled into a cylindrical shape and inserted into a specific surface area measuring cell. The loaded sample weight at this time is preferably about 0.20 to 0.60 g. The sample-loaded cell was dried for 30 minutes under conditions of 60° C., and cooled for 10 minutes. Next, the cell was set in the specific surface area measuring apparatus, and with nitrogen gas adsorption on the sample surface, the following BET formula:

$$P/(V(P0-P))=1/(Vm \times C)+((C-1)/(Vm \times C))(P/P0)$$

{where P0: saturated water vapor pressure (Pa), Vm: monolayer adsorption (mg/g), C: parameter (−)<0 relating to adsorption heat, this relational expression usually holds, especially when P/P0=0.05 to 0.35} was applied to determine the specific surface area value. A BET formula is a formula expressing the relationship between adsorption equilibrium pressure P and adsorption V at that pressure, at a constant temperature and at adsorption equilibrium.

(8) Measurement of Tensile Force (N/25 mm)

Following the method of JIS 8113, 10 cm on each end of the nonwoven fabric was removed, the 25 mm width×200 mm length test piece was gripped and anchored with an chuck distance of 100 mm, and measurement was performed at a cross head speed of 20 mm/min. Five samples were taken from every 1 m of nonwoven fabric width. A load was applied until the test piece fractured, and the average value of the strength of the test piece at maximum load in the machine direction (MD) and the cross-machine direction (CD) was calculated.

(9) Gurley Air Permeability (sec/100 ml)

A Gurley densometer ("B" type by Yasuda Seiki Seisakusho Co., Ltd.) was used for measurement of the permeation time for 100 ml of air (units: s/100 ml), at room temperature. Measurement was conducted at 5 points at different locations of each nonwoven fabric sample, and the average value was recorded as the air permeability.

(10) Puncture Strength (N)

A needle with a diameter of φ25 mm and a tip radius of 12.5 mm was mounted in a benchtop precision universal testing machine (Model AGS-1000D by Shimadzu Corp.), and a puncture test was conducted at a temperature of 23±2° C. and a needle traveling speed of 50 mm/min. Measurement was conducted at 5 points at different locations of each nonwoven fabric sample, and the average value was recorded as the puncture strength.

(11) Heat Sealability

The heat seal strength after heat sealing at an appropriate temperature was measured by the following method, according to JIS L 1086. Two sample strips of 10 cm length, 3 cm width were stacked, while heat sealing portions 2 cm from the ends parallel to the cross-machine direction of the sample strip, and 5 such samples were prepared. The heat sealing was carried out using a hot press machine having an upper and lower pair of pressure welding bars (1 cm width, 30 cm length) coated with polytetrafluoroethylene, for 1 second at a contact pressure of 98 N/cm². Next, using a benchtop precision universal testing machine (Model AGS-1000D by Shimadzu Corp.), the sample was set so that the bonded section was at the center of a chuck with a grip spacing of 7 cm and peeled at a pull rate of 10 cm/min, and the three largest maximum values and the three smallest minimum values exhibited during peeling were taken, recording the average value of the total of 6 values as the heat sealability.

(12) Peeling Property

A sheet (unstretched polypropylene obtained by a T-die method) was attached to each of the packaging materials obtained in Examples 1 to 14 by an appropriate method, and the peeling property, upon peeling of the sheet from the sterilized sheet after high-pressure steam sterilization processing, was judged by visual assessment of the amount of fluff transferred to the sheet after peeling. The peeling property after high-pressure steam sterilization processing for Comparative Examples 4 and 5 was evaluated as VG, with two levels for lower properties: a lower property as G and an even lower property as P.

(13) Water Pressure Resistance

After removing 10 cm at both ends of each of the packaging materials obtained in Examples 1 to 14, 20 cm-square test pieces were sampled from 5 equal portions in the CD direction and 3 equal portions in the MD direction, for a total of 15, they were measured according to JIS L 1092, and the water pressure resistance was calculated from the average of the measured values.

(14) Heat Shrinkage Factor

A 80 mm×80 mm square mark is made in a 300 mm length, 210 mm width sample, and the dimensions are measured. The sample with the square mark is held for 15 minutes in a dry heater set to a temperature of 125° C., the dimensions of the square are measured and compared with those before placement in the dry heater, and the shrinkage factor is calculated.

(15) Cell Property Evaluation

This is conducted according to a bacteriocidal test method under voluntary standards for disposable medical tool packaging materials. Dry fine powder is prepared by obtaining non-sandy dirt from a river bed or the like, allowing it to naturally dry away from heat and sunlight, and then preparing fine powder using a mortar. Measurement is then performed, and a sample with an environmental bacteria group of at least $10^4$ cells/g is used. Six packaging materials for sterilization are prepared, being sealed on 3 sides and each having a size sufficient to allow housing of a 9 cm diameter shallow dish, and each is pre-sterilized. The sterilization method employed is a method that does not produce degeneration of the bag during sterilization processing. The cover of an agar plate culture medium prepared by a common method is removed, and it is placed inside and sealed. Three of the three-way sealed materials are used as samples, and the remaining three are used as control samples. For a control test, holes are formed at 3 locations using a 24-gauge needle (outer diameter: 0.54 to 0.58 mm). Approximately 10 g of gold-containing dry fine powder is placed at the bottom of a reduced pressure desiccator, 3 each of the samples and control samples in the dishes are placed in the desiccator and then brought to a degree of vacuum of 560 mmHg (−200 mmHg below atmospheric pressure), and after maintaining this for approximately 3 minutes, the cock is fully opened to attack and air is introduced causing sufficient floating of the fine powder, and the system is restored to atmospheric pressure. Next, the samples and control samples are removed from the desiccator, and after 48 hours of culturing at 37 degrees, it is confirmed whether visible colonies are present in the control samples, and whether visible colonies are present in the samples. A 2-level assessment was made, with G if no colonies were present, and P if they were present.

(16) Atmospheric Dust Trapping Efficiency

The atmosphere was trapped before and after passing through a measuring device, using a measuring area of 78.5 cm² (diameter: 10 cm) and a wind speed of 23.0 L/min, 1 µm particles (dust) in the trapped atmosphere were measured using a particle counter (Rion Co., Ltd.), and calculation was performed by the following formula.

Atmospheric dust trapping efficiency (%)=[1−(number of downstream particles/number of upstream particles)]×100

EXAMPLES 1 TO 7

Using a polyethylene terephthalate (PET) resin in a spunbond method, a long fiber group of filaments was extruded toward a moving collection net and spun at a spinning speed of 4500 m/min, at a spinning temperature of 300° C., electrification was carried out at about 3 µC/g by corona electrification to thoroughly open the fibers, and a thermoplastic resin long fiber web was formed on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PET resin melting temperature, spinning gas temperature and molten resin single-hole throughput in the extruder were appropriately selected for tow thinning of the thermoplastic resin. An SB nonwoven fabric was also blown onto the MB nonwoven fabric in the same manner to produce an SB-MB-SB layered nonwoven fabric. The obtained web was then calendered to obtain a packaging material for sterilization.

EXAMPLE 8

Using a PET resin in a spunbond method, a long fiber group of filaments was extruded toward a moving collection net and spun at a spinning speed of 4500 m/min, at a spinning temperature of 300° C., electrification was carried out at about 3 µC/g by corona electrification to thoroughly open the fibers, and a thermoplastic resin long fiber web was formed on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PET resin melting temperature, spinning gas temperature and molten resin single-hole throughput in the extruder were appropriately selected for tow thinning of the thermoplastic resin, to produce an SB-MB layered nonwoven fabric. The obtained web was then calendered to obtain a packaging material for sterilization.

EXAMPLES 9 TO 12

Using a polypropylene (PP) resin in a spunbond method, a long fiber group of filaments was extruded toward a moving collection net and spun at a spinning speed of 4500 m/min, at a spinning temperature of 230° C., electrification was carried out at about 3 µC/g by corona electrification to thoroughly open the fibers, and a thermoplastic resin long fiber web was formed on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PP resin melting temperature, spinning gas temperature and molten resin single-hole throughput in the extruder were appropriately selected for tow thinning of the thermoplastic resin. An SB nonwoven fabric was also blown onto the MB nonwoven fabric in the same manner to produce an SB-MB-SB layered nonwoven fabric. The obtained web was then calendered to obtain a packaging material for sterilization.

EXAMPLE 13

Using a PET resin in a spunbond method, a long fiber group of filaments was extruded toward a moving collection net and spun at a spinning speed of 4500 m/min, at a spinning temperature of 300° C., electrification was carried out at about 3 µC/g by corona electrification to thoroughly open the fibers, and a thermoplastic resin long fiber web was formed on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PET resin melting temperature, spinning gas temperature and molten resin single-hole throughput in the extruder were appropriately selected for tow thinning of the thermoplastic resin. An SB nonwoven fabric was also blown onto the MB nonwoven fabric in the same manner to produce an SB-MB-SB layered nonwoven fabric. The obtained web was then calendered, and subjected to water repellency treatment by coating with a fluorine-based water-repellent agent by an appropriate method.

EXAMPLE 14

Using a PET resin and a CO-PET resin in a spunbond method, a long fiber group of filaments was extruded toward a moving collection net and spun at a spinning speed of 4500 m/min, at a spinning temperature of 300° C., electrification was carried out at about 3 µC/g by corona electrification to thoroughly open the fibers, and a thermoplastic resin long fiber web was formed as a two-component fiber nonwoven fabric on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PET resin melting temperature, spinning gas temperature and molten resin single-hole throughput in the extruder were appropriately selected for tow thinning of the thermoplastic resin. An SB nonwoven fabric was also blown onto the MB nonwoven fabric in the same manner to produce an SB-MB-SB layered nonwoven fabric. The obtained web was then calendered to obtain a packaging material for sterilization.

EXAMPLES 15 TO 22

Using a polyethylene terephthalate (PET) resin in a spunbond method, in the same manner as Examples 1 to 7, a long fiber group of filaments was extruded toward a moving collection net and spun at a spinning speed of 4500 m/min, at a spinning temperature of 300° C., electrification was carried out at about 3 µC/g by corona electrification to thoroughly open the fibers, and a thermoplastic resin long fiber web was formed on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PET resin melting temperature, spinning gas temperature and molten resin single-hole throughput in the extruder were appropriately selected for tow thinning of the thermoplastic resin. An SB nonwoven fabric was also blown onto the MB nonwoven fabric in the same manner to produce an SB-MB-SB layered nonwoven fabric. The conditions for discharge, cooling and trapping during discharge were each set from the viewpoint of minimizing fusion. The obtained web was then subjected to calendering under appropriate conditions using calender rolls with optimized roll hardness, from the viewpoint of maintaining the fiber shapes, to obtain a packaging material for sterilization.

EXAMPLE 23

Using a polypropylene (PP) resin in a spunbond method, in the same manner as Examples 1 to 7, a long fiber group of filaments was extruded toward a moving collection net and spun at a spinning speed of 4500 m/min, at a spinning temperature of 230° C., electrification was carried out at about 3 µC/g by corona electrification to thoroughly open the fibers, and a thermoplastic resin long fiber web was formed on the collection net. The web was blown by the MB method described below onto the previously formed SB nonwoven fabric. Using a PET resin as the fiber material, the molten PET resin was extruded with an extruder from a spinneret nozzle with a spinneret nozzle diameter of 0.30 mm. The PP resin melting temperature, spinning gas temperature and molten resin single-hole throughput in the extruder were appropriately selected for tow thinning of the thermoplastic resin. An SB nonwoven fabric was also blown onto the MB nonwoven fabric in the same manner to produce an SB-MB-SB layered nonwoven fabric. The conditions for discharge, cooling and trapping during discharge were each set from the viewpoint of minimizing fusion. The obtained web was then subjected to calendering under appropriate conditions using calender rolls with optimized roll hardness, from the viewpoint of maintaining the fiber shapes, to obtain a packaging material for sterilization.

COMPARATIVE EXAMPLE 1

A nonwoven fabric (yam diameter: 16 µm, basis weight: 25 g/m$^2$) made of a PET resin was blown onto a net by an SB method, and thermally bonded with flat rolls at a linear pressure of 260 N/cm and a temperature of 190° C., and then processed with calender rolls at a linear pressure of 294 N/cm and a temperature of 245° C., to obtain a layered nonwoven fabric.

COMPARATIVE EXAMPLE 2

An MB nonwoven fabric (yam diameter: 2 µm, basis weight: 25 g/m$^2$) made of a PET resin was blown onto a net and thermally bonded with flat rolls at a linear pressure of 260 N/cm and a temperature of 120° C., and then processed with calender rolls at a linear pressure of 340 N/cm and a temperature of 40° C., to obtain a layered nonwoven fabric.

COMPARATIVE EXAMPLE 3

An MB nonwoven fabric (yarn diameter: 1.0 μm, basis weight: 25 g/m²) made of a PET resin was blown onto a net, and then processed with calender rolls at a linear pressure of 340 N/cm and a temperature of 40° C., to obtain a layered nonwoven fabric.

COMPARATIVE EXAMPLE 4

A packaging material for sterilization composed of a nonwoven fabric formed by a commonly used polyethylene flash spun method (yarn diameter: 5 μm, basis weight: 75 g/m²).

COMPARATIVE EXAMPLE 5

A packaging material for sterilization composed of a nonwoven fabric formed by a commonly used polyethylene flash spun method (yarn diameter: 4 μm, basis weight: 63 g/m²).

COMPARATIVE EXAMPLE 6

A sterilized sheet composed of commonly used pulp staple fibers (yarn diameter: 4 μm, basis weight: 63 g/m²).

The nonwoven fabric structures of Examples 1 to 23 and Comparative Examples 1 to 6, and the specific properties of the obtained nonwoven fabrics, are shown in Tables 1 to 4 below.

TABLE 1

| | Layer I | | | Layer II Prescription | | | | Layer I | | | |
|---|---|---|---|---|---|---|---|---|---|---|---|
| | Fiber type | Fiber diameter | Fiber amount | Fiber type | Fiber diameter | Specific surface area | Fiber amount | Fiber type | Fiber diameter | Fiber amount | Melting point |
| Units | | μm | g/m² | | μm | | g/m² | | μm | g/m² | ° C. |
| Example 1 | PET SB | 12 | 20 | PET MB | 0.3 | 3.0 | 10 | PET SB | 12 | 20 | 260 |
| Example 2 | PET SB | 20 | 20 | PET MB | 1.1 | 1.9 | 10 | PET SB | 20 | 20 | 260 |
| Example 3 | PET SB | 20 | 20 | PET MB | 2.1 | 0.9 | 10 | PET SB | 20 | 20 | 260 |
| Example 4 | PET SB | 20 | 20 | PET MB | 3.1 | 0.7 | 10 | PET SB | 20 | 20 | 260 |
| Example 5 | PET SB | 12 | 35 | PET MB | 2.4 | 0.7 | 10 | PET SB | 12 | 35 | 260 |
| Example 6 | PET SB | 12 | 20 | PET MB | 2.6 | 0.6 | 5 | PET SB | 12 | 20 | 260 |
| Example 7 | PET SB | 12 | 20 | PET MB | 2.2 | 0.9 | 30 | PET SB | 12 | 20 | 260 |
| Example 8 | PET SB | 15 | 20 | PET MB | 2.0 | 1.0 | 10 | — | — | — | — |
| Example 9 | PP SB | 12 | 20 | PP MB | 0.1 | 8.0 | 10 | PP SB | 12 | 20 | 160 |
| Example 10 | PP SB | 15 | 20 | PP MB | 1.0 | 2.8 | 10 | PP SB | 15 | 20 | 160 |
| Example 11 | PP SB | 15 | 20 | PP MB | 1.2 | 2.5 | 10 | PP SB | 15 | 20 | 160 |
| Example 12 | PP SB | 15 | 20 | PP MB | 1.6 | 2.0 | 20 | PP SB | 15 | 20 | 160 |
| Example 13 | PET SB | 12 | 20 | PET MB | 2.1 | 1.6 | 10 | PET SB | 12 | 20 | 260 |
| Example 14 | Co-PET/PET SB | 20 | 20 | PET MB | 2.4 | 1.5 | 10 | PET SB | 15 | 20 | 260 |

TABLE 2

| | Prescription | | | | | | | | | |
|---|---|---|---|---|---|---|---|---|---|---|
| | Basis weight | Thickness | Density | Void % | MD tensile strength | CD tensile strength | Average flow rate pore diameter | Bubble point | Specific surface area | Heat shielding property |
| Units | g/m² | μm | g/cm³ | % | N/25 mm | N/25 mm | μm | μm | m²/g | N/3 cm |
| Example 1 | 50 | 0.08 | 0.66 | 52 | 52.2 | 22.5 | 1.4 | 5.4 | 0.08 | 32 |
| Example 2 | 50 | 0.07 | 0.71 | 48 | 54 | 23 | 1.9 | 8.0 | 0.04 | 39 |
| Example 3 | 51 | 0.06 | 0.85 | 39 | 73 | 27 | 3.4 | 10.8 | 0.02 | 38 |
| Example 4 | 51 | 0.06 | 0.86 | 38 | 74 | 28 | 4.8 | 14.7 | 0.03 | 41 |
| Example 5 | 30 | 0.04 | 0.76 | 45 | 20 | 45 | 4.0 | 9.0 | 0.03 | 37 |

TABLE 2-continued

| | | | | | | | | | | |
|---|---|---|---|---|---|---|---|---|---|---|
| Example 6 | 60 | 0.06 | 1.01 | 27 | 87 | 39 | 17.4 | 38.2 | 0.02 | 33 |
| Example 7 | 80 | 0.08 | 1.00 | 27 | 81 | 41 | 2.8 | 3.0 | 0.04 | 31 |
| Example 8 | 30 | 0.03 | 0.99 | 28 | 17 | 39 | 11.3 | 23.4 | 0.04 | 38 |
| Example 9 | 45 | 0.16 | 0.28 | 69 | 12.3 | 5.8 | 1.4 | 10.5 | 0.09 | 31 |
| Example 10 | 51 | 0.08 | 0.63 | 30 | 14 | 30 | 1.2 | 4.3 | 0.04 | 30 |
| Example 11 | 55 | 0.10 | 0.55 | 39 | 35 | 18 | 2.1 | 7.3 | 0.06 | 32 |
| Example 12 | 66 | 0.11 | 0.60 | 33 | 28 | 15 | 1.0 | | 0.06 | 32 |
| Example 13 | 50 | 0.06 | 0.83 | 40 | 74 | 35 | 2.8 | 9.0 | 0.02 | 36 |
| Example 14 | 52 | 0.06 | 0.87 | 37 | 70 | 30 | 3.5 | 20.2 | 0.02 | 53 |

| | Prescription | | | | | | | | |
|---|---|---|---|---|---|---|---|---|---|
| | Gurley air permeability | Puncture strength | MD tearing strength | CD tearing strength | Steam permeability | Heat shrinkage | Water pressure resistance | Cell property evaluation | Atmospheric dust trapping efficiency |
| Units | sec | N | N | N | g/m²/24 hr | % | mmH₂O | | % |
| Example 1 | 5 | 237 | 17 | 24 | 1680 | 0.6 | 260 | G | 95.4 |
| Example 2 | 3 | 259 | 15 | 22 | 1700 | 0.6 | 310 | G | 94.3 |
| Example 3 | 5 | 257 | 17 | 19 | 1650 | 0.5 | 290 | G | 93.2 |
| Example 4 | 3 | 269 | 13 | 22 | 1710 | 0.5 | 220 | G | 92.8 |
| Example 5 | 3 | 576 | 32 | 31 | 1730 | 0.4 | 1530 | G | 92.6 |
| Example 6 | 15 | 240 | 13 | 22 | 1350 | 0.3 | 390 | G | 90.2 |
| Example 7 | 27 | 242 | 14 | 29 | 1230 | 0.4 | 500 | G | 91.8 |
| Example 8 | 1 | 174 | 11 | 6 | 1920 | 0.5 | 350 | G | 90.9 |
| Example 9 | 2 | 224 | 21 | 26 | 1850 | 0.6 | 910 | G | 95.8 |
| Example 10 | 11 | 248 | 14 | 30 | 1410 | 0.7 | 610 | G | 93.9 |
| Example 11 | 4 | 268 | 26 | 26 | 1780 | 0.8 | 550 | G | 92.1 |
| Example 12 | 12 | 249 | 23 | 33 | 1400 | 0.9 | 530 | G | 94.6 |
| Example 13 | 7 | 257 | 25 | 19 | 1660 | 0.5 | 710 | G | 91.4 |
| Example 14 | 4 | 360 | 16 | 20 | 1800 | 0.9 | 980 | G | 91.9 |

TABLE 3

| | Layer I | | | Layer II Prescription | | | Layer I | | | |
|---|---|---|---|---|---|---|---|---|---|---|
| | Fiber type | Fiber diameter | Fiber amount | Fiber type | Fiber diameter | Specific surface area | Fiber amount | Fiber type | Fiber diameter | Fiber amount | Melting point |
| Units | | μm | g/m² | | μm | | g/m² | | μm | g/m² | °C. |
| Example 15 | PET SB | 12 | 20 | PET MB | 0.3 | 6.2 | 10 | PET SB | 12 | 20 | 260 |
| Example 16 | PET SB | 12 | 20 | PET MB | 0.1 | 12.1 | 10 | PET SB | 12 | 20 | 260 |
| Example 17 | PET SB | 20 | 20 | PET MB | 1.1 | 5.8 | 10 | PET SB | 20 | 20 | 260 |
| Example 18 | PET SB | 20 | 20 | PET MB | 2.1 | 3.9 | 10 | PET SB | 20 | 20 | 260 |
| Example 19 | PET SB | 20 | 20 | PET MB | 3.1 | 2.8 | 10 | PET SB | 20 | 20 | 260 |
| Example 20 | PET SB | 12 | 35 | PET MB | 2.4 | 1.8 | 10 | PET SB | 12 | 35 | 260 |
| Example 21 | PET SB | 12 | 20 | PET MB | 2.6 | 2.5 | 5 | PET SB | 12 | 20 | 260 |
| Example 22 | PET SB | 12 | 20 | PET MB | 2.2 | 2.0 | 30 | PET SB | 12 | 20 | 260 |
| Example 23 | PP SB | 12 | 20 | PP MB | 0.1 | 15.1 | 10 | PP SB | 12 | 20 | 160 |
| Comp. Example 1 | PET SB | 16 | 25 | — | — | — | — | — | — | — | — |
| Comp. Example 2 | — | — | — | PET MB | 2 | 1.3 | 25 | — | — | — | — |
| Comp. Example 3 | — | — | — | PET MB | 1 | 2.2 | 25 | — | — | — | — |
| Comp. Example 4 | — | — | — | PE Flash-spun | 5 | 0.8 | 73.5 | — | — | — | — |

TABLE 3-continued

| | Layer I | | | Layer II Prescription | | | | Layer I | | |
|---|---|---|---|---|---|---|---|---|---|---|
| | Fiber type | Fiber diameter | Fiber amount | Fiber type | Fiber diameter | Specific surface area Units | Fiber amount | Fiber type | Fiber diameter | Fiber amount | Melting point |
| | | μm | g/m² | | μm | | g/m² | | μm | g/m² | ° C. |
| Comp. Example 5 | — | — | — | PE Flash-spun | 4 | 1.1 | 62.5 | — | — | — | — |
| Comp. Example 6 | — | — | — | Pulp staple fibers | 22 | 0.5 | 62.6 | — | — | — | — |

TABLE 4

| | Perscription | | | | | | | | | | |
|---|---|---|---|---|---|---|---|---|---|---|---|
| | Basis weight | Thickness | Density | Void % | MD tensile strength | CD tensile strength Unit | Average flow rate pore diameter | Bubble point | Specific surface area | Heat shielding property |
| | g/m² | μm | g/cm³ | % | N/25 mm | N/25 mm | μm | μm | m²/g | N/3 cm |
| Example 15 | 50 | 0.08 | 0.66 | 52 | 50.1 | 23.5 | 1.3 | 5.8 | 1.2 | 30 |
| Example 16 | 50 | 0.08 | 0.63 | 55 | 51.5 | 25.6 | 0.6 | 3.1 | 2.8 | 30 |
| Example 17 | 50 | 0.07 | 0.71 | 48 | 52 | 20 | 1.8 | 7.8 | 0.9 | 41 |
| Example 18 | 51 | 0.06 | 0.85 | 39 | 75 | 24 | 3.2 | 11.9 | 0.5 | 40 |
| Example 19 | 51 | 0.05 | 1.03 | 26 | 78 | 29 | 4.2 | 15.1 | 0.4 | 43 |
| Example 20 | 30 | 0.05 | 0.60 | 56 | 25 | 44 | 3.8 | 10.5 | 0.3 | 40 |
| Example 21 | 60 | 0.08 | 0.75 | 45 | 67 | 42 | 14.3 | 35.6 | 0.4 | 39 |
| Example 22 | 80 | 0.1 | 0.80 | 42 | 84 | 48 | 1.9 | 2.9 | 0.5 | 32 |
| Example 23 | 45 | 0.16 | 0.28 | 69 | 12.3 | 5.8 | 1.4 | 10.5 | 3.0 | 31 |
| Comp. Example 1 | 25 | 0.04 | 0.59 | 57 | 78 | 39 | 35.3 | 87.8 | — | 12 |
| Comp. Example 2 | 25 | 0.04 | 0.66 | 52 | 5 | 2 | 3.9 | 9.7 | 1.3 | 21 |
| Comp. Example 3 | 25 | 0.04 | 0.60 | 57 | 4 | 2 | 1.8 | 5.9 | 2.2 | 29 |
| Comp. Example 4 | 74 | 0.17 | 0.43 | 52 | 239 | 222 | 1.9 | 7.2 | 0.8 | 25 |
| Comp. Example 5 | 63 | 0.14 | 0.45 | 50 | 148 | 229 | 1.9 | 7.3 | 1.1 | 22 |
| Comp. Example 6 | 63 | 0.09 | 0.70 | — | 178 | 92 | 2.9 | 10.5 | 0.5 | 28 |

| | Perscription | | | | | | | | |
|---|---|---|---|---|---|---|---|---|---|
| | Gurley air permeability | Puncture strength | MD tearing strength | CD tearing strength | Steam permeability Unit | Heat shrinkage | Water pressure resistance | Cell property evaluation | Atmospheric dust trapping efficiency |
| | sec | N | N | N | g/m²/24 hr | % | mmH₂O | | % |
| Example 15 | 5 | 241 | 18 | 29 | 1640 | 0.6 | 270 | G | 99.8 |
| Example 16 | 11 | 254 | 19 | 28 | 1460 | 5.0 | 350 | G | 99.9 |
| Example 17 | 4 | 248 | 17 | 25 | 1740 | 0.7 | 320 | G | 98.1 |
| Example 18 | 5 | 261 | 18 | 21 | 1640 | 0.6 | 300 | G | 96.5 |
| Example 19 | 4 | 271 | 18 | 21 | 1700 | 0.7 | 230 | G | 95.4 |
| Example 20 | 5 | 581 | 30 | 35 | 1720 | 0.4 | 1500 | G | 93.2 |
| Example 21 | 11 | 262 | 15 | 29 | 1340 | 0.3 | 400 | G | 94.5 |
| Example 22 | 22 | 251 | 19 | 38 | 1130 | 0.4 | 510 | G | 96.8 |
| Example 23 | 2 | 224 | 21 | 26 | 1850 | 0.6 | 910 | G | 99.9 |
| Comp. Example 1 | 0.3 | 119 | 9 | 8 | 2420 | 0.7 | 100 | P | 35.2 |
| Comp. Example 2 | 29 | 11 | 2 | 2 | 340 | 0.5 | 70 | G | 99.8 |
| Comp. Example 3 | 35 | 9 | 3 | 2 | 300 | 0.6 | 80 | G | 99.9 |
| Comp. Example 4 | 14.7 | 568 | 3 | 4 | 1620 | 7.0 | 1500 | G | 99.9 |

TABLE 4-continued

| | | | | | | | | | |
|---|---|---|---|---|---|---|---|---|---|
| Comp. Example 5 | 16.2 | 341 | 5 | 2 | 1600 | 7.5 | 1450 | G | 99.9 |
| Comp. Example 6 | 10.4 | 53 | 1 | 1 | 530 | 2.0 | 340 | G | 85.4 |

INDUSTRIAL APPLICABILITY

The layered nonwoven fabric of the invention can be suitably used as a packaging material for sterilization in the field of medicine, for the purpose of preventing infectious contamination of sondes, scalpels, pincettes, scissors and the like.

The invention claimed is:

1. A packaging material for sterilization constructed of a layered nonwoven fabric with at least two layers, comprising a nonwoven fabric layer (I) formed of continuous long fibers having an average fiber diameter of 5 to 30 µm and a nonwoven fabric layer (II) formed of ultrafine fibers having an average fiber diameter of 0.1 to 4 µm, wherein the specific surface area of the packaging material is 1.2 to 10 m$^2$/g, and the apparent density of the packaging material is 0.66 g/cm$^3$ or less.

2. The packaging material for sterilization according to claim 1, wherein an interlayer formed of the nonwoven fabric layer (II) is disposed between two layers of the nonwoven fabric layer (I).

3. The packaging material for sterilization according to claim 1, wherein the nonwoven fabric layer (II) is composed of a melt-blown nonwoven fabric.

4. The packaging material for sterilization according to claim 1, wherein the average flow pore size of the layered nonwoven fabric is 0.1 to 30 µm, and the bubble point is 0.5 to 50 µm.

5. The packaging material for sterilization according to claim 1, wherein the basis weight of the layered nonwoven fabric is 8.0 to 100 g/m$^2$, and the thickness is 0.03 to 0.2 mm.

6. The packaging material for sterilization according to claim 1, wherein the air permeability is 1 to 100 seconds/100 ml, as determined by the time required for 100 ml of air to pass through the layered nonwoven fabric in a Gurley air permeability test.

7. The packaging material for sterilization according to claim 1, wherein the tensile strength of the layered nonwoven fabric is 10 to 300 N/25 mm width, and the puncture strength is 70 to 700 N.

8. The packaging material for sterilization according to claim 1, wherein the layered nonwoven fabric is made of polyester.

9. The packaging material for sterilization according to claim 2, wherein the nonwoven fabric layer (II) is composed of a melt-blown nonwoven fabric.

10. The packaging material for sterilization according to claim 2, wherein the average flow pore size of the layered nonwoven fabric is 0.1 to 30 µm, and the bubble point is 0.5 to 50 µm.

11. The packaging material for sterilization according to claim 2, wherein the basis weight of the layered nonwoven fabric is 8.0 to 100 g/m$^2$, and the thickness is 0.03 to 0.2 mm.

12. The packaging material for sterilization according to claim 2, wherein the air permeability is 1 to 100 seconds/100 ml, as determined by the time required for 100 ml of air to pass through the layered nonwoven fabric in a Gurley air permeability test.

13. The packaging material for sterilization according to claim 2, wherein the tensile strength of the layered nonwoven fabric is 10 to 300 N/25 mm width, and the puncture strength is 70 to 700 N.

14. The packaging material for sterilization according to claim 2, wherein the layered nonwoven fabric is made of polyester.

15. The packaging material for sterilization according to claim 1, wherein the atmospheric dust trapping efficiency is 98.1% to 99.9%.

16. The packaging material for sterilization according to claim 15, wherein the specific surface area of the packaging material is 1.2 to 3 m$^2$/g.

17. The packaging material for sterilization according to claim 1, wherein the specific surface area of the packaging material is 1.2 to 3 m$^2$/g.

18. The packaging material for sterilization according to claim 1, wherein the specific surface area of the nonwoven fabric layer (II) is 1.8 to 15.1 m$^2$/g.

19. The packaging material for sterilization according to claim 15, wherein the specific surface area of the nonwoven fabric layer (II) is 1.8 to 15.1 m$^2$/g.

* * * * *